United States Patent [19]

Schultz et al.

[11] Patent Number: 4,921,492
[45] Date of Patent: May 1, 1990

[54] END EFFECTOR FOR SURGICAL PLUME EVACUATOR

[75] Inventors: Leonard S. Schultz, Minneapolis, Minn.; Jay F. Gold, Yonkers, N.Y.; Rodney V. Erdman, Princeton, Minn.

[73] Assignee: Laser Technologies Group, Inc., Minneapolis, Minn.

[21] Appl. No.: 200,405

[22] Filed: May 31, 1988

[51] Int. Cl.⁵ ............................................. A61M 1/00
[52] U.S. Cl. ................................... 604/315; 604/317; 128/888
[58] Field of Search .................... 600/21; 128/38, 760, 128/888, 897, 846, 847, 863; 604/35, 73, 119, 129, 313, 315, 316, 317, 327, 332, 355

[56] References Cited

U.S. PATENT DOCUMENTS

| | | |
|---|---|---|
| Re. 29,319 | 7/1977 | Norbdy et al. . |
| 452,131 | 5/1891 | Haughawout . |
| 2,195,771 | 4/1940 | Estler . |
| 2,305,289 | 12/1942 | Coburg ........................... 128/847 |
| 2,524,750 | 10/1950 | Bellinger . |
| 3,026,874 | 3/1962 | Stevens ........................... 128/888 |
| 3,315,665 | 4/1967 | MacLeod . |
| 3,568,675 | 3/1971 | Harvey ............................ 604/355 |
| 3,610,238 | 10/1971 | Rich, Jr. ......................... 128/847 |
| 3,763,857 | 10/1973 | Schrading ........................ 128/847 |
| 4,082,092 | 4/1978 | Foster . |
| 4,250,882 | 2/1981 | Adair . |
| 4,469,092 | 9/1984 | Marshall et al. . |
| 4,533,352 | 8/1985 | Van Beek et al. . |
| 4,553,967 | 11/1985 | Ferguson et al. ................ 604/317 |
| 4,735,603 | 4/1988 | Goodson et al. . |
| 4,778,446 | 10/1988 | Jensen ............................. 604/317 |
| 4,787,894 | 11/1988 | Turnbull ......................... 604/319 |
| 4,795,435 | 1/1989 | Steer .............................. 604/332 |
| 4,834,110 | 5/1989 | Richard .......................... 604/327 |

*Primary Examiner*—Stephen C. Pellegrino
*Assistant Examiner*—Ralph Lewis
*Attorney, Agent, or Firm*—Dorsey & Whitney

[57] ABSTRACT

An end effector for efficiently removing the gaseous byproducts of laser surgery from a surgical site is provided. The end effector includes a flexible hose and a pliable vacuum head adhesively attachable in airtight relationship around a surgical site. The vacuum head includes a generally annular plenum for drawing plumes away from the surgical site from around a 360° arc. A porous plenum support prevents the flexible plenum from collapsing in the presence of a vacuum, and diffuses the vacuum around the entire periphery of the plenum.

10 Claims, 2 Drawing Sheets

4,921,492

END EFFECTOR FOR SURGICAL PLUME EVACUATOR

TECHNICAL FIELD

This invention relates to equipment for the removal of the gaseous byproducts of laser surgery. In particular, it relates to an end effector for a vacuum filtration system that efficiently removes smoke plumes produced through the use of lasers at a surgical site.

BACKGROUND ART

The use of lasers in surgical operations has become commonplace. An unwanted byproduct of laser surgery, however, is the smoke generated by interaction of the laser with skin and muscle tissues. Smoke plumes so caused can obscure the surgeon's field of vision, and the odor generated is unpleasant and distracting to the entire surgical team. Moreover, the smoke plume may contain infectious agents that present an immediate danger to persons in the operating room, and which can leave a lingering contamination within the operating area.

Evacuation filtering systems have been developed to remove smoke plumes from laser surgical sites. Such systems typically include a hose connected to a vacuum generator. Various filtration systems have been used in conjunction with such vacuum generators to remove odor and infectious agents. Heretofore, the hoses of plume evacuation and filtration systems have required the constant attention of an attendant to hold the nozzle of the hose close to the surgical site. Moreover, the flow of air through the hose nozzle is a source of excessive and unwanted noise in the operating room.

An end effector for a surgical plume evacuator that could be held in place at a surgical site without the constant attention of a nurse or other attendant, and which could efficiently, completely, and quietly remove smoke plumes from the area of the surgical site, would be a decided advantage.

SUMMARY OF THE INVENTION

The problems outlined above are in large measure solved by the surgical plume evacuator end effector in accordance with the present invention. The end effector hereof can be maintained at a laser surgery site without constant manipulation by an attendant, and is especially designed to completely, efficiently, and quietly remove the smoke plumes generated in the process of laser surgery.

The plume evacuator end effector hereof broadly includes an evacuation hose adapted for detachable connection to a vacuum generator having an environmental filter, and a vacuum head that completely surrounds a surgical site. The vacuum head is made of a pliable material and defines an evacuation plenum. A porous plenum supporting material is carried within the plenum to provide rigidity to the plenum and to prevent the plenum from collapsing when subjected to a vacuum. An adhesive layer is carried by the bottom wall of the vacuum head for maintaining the head in place at a surgical site.

DETAILED DESCRIPTION OF THE DRAWINGS

Figure 1:
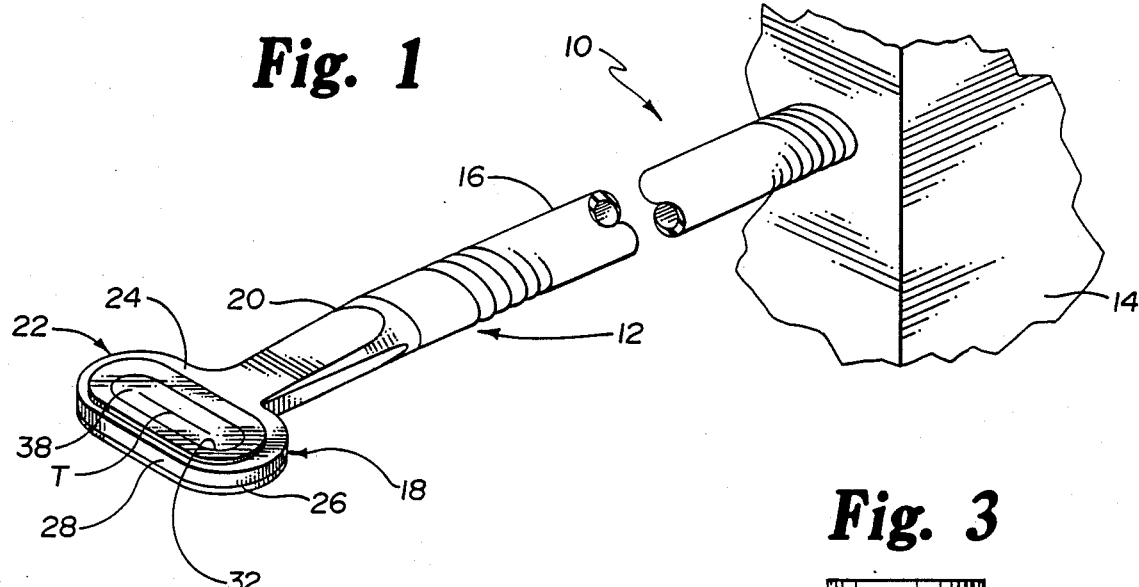
FIG. 1 is a fragmentary, perspective view of a surgical plume evacuator having an end effector in accordance with the present invention.

Referring to the drawings, a plume evacuation system 10 having an end effector 12 in accordance with the present invention is depicted in FIG. 1. The end effector 12 is shown detachably connected to a vacuum generator and filtration assembly 14. The vacuum/filtration system typically includes a vacuum generator motor and an environmental filter (both not shown). Air is cycled into the vacuum generator 14 through the end effector 12, is filtered to remove odors and infectious agents, and is returned to the environment. A typical filtration assembly could include a prefilter to remove large contaminants, a charcoal filter to remove odors, and a HEPA (High Efficiency Particle Accumulator) filter to remove infectious agents.

End effector 12 broadly includes a flexible hose 16 coupled to a vacuum head 18 by a generally tubular handle 20. The length of hose 16 can vary according to need, but would typically be from six to eight feet. The surface of hose 18 is preferably corrugated along its length to provide the hose 18 with cross sectional rigidity while allowing for axial flexibility.

Vacuum head 16 includes a generally flat collector 22 having a collector top wall 24, collector bottom wall 26 and collector sidewall 28 extending between the collector top wall 24 and collector bottom wall 26. The collector 22 is preferably formed from a nonporous, pliable synthetic resin. The collector top, bottom, and sidewalls 24, 26, 28 together define a generally annular, internal plenum 30.

Figure 2:
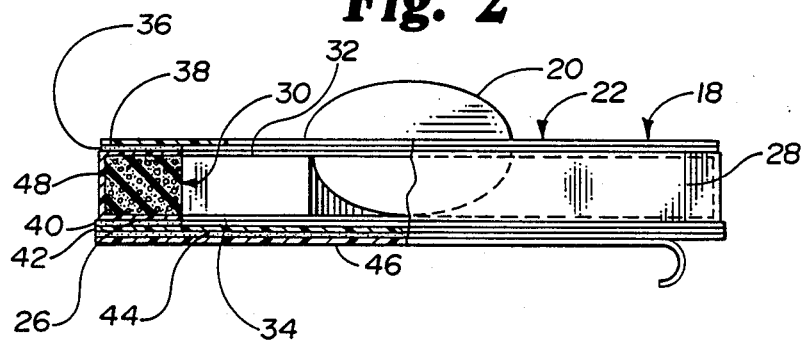
FIG. 2 is a front elevational view of the end effector, with parts broken away for clarity.
Figure 3:
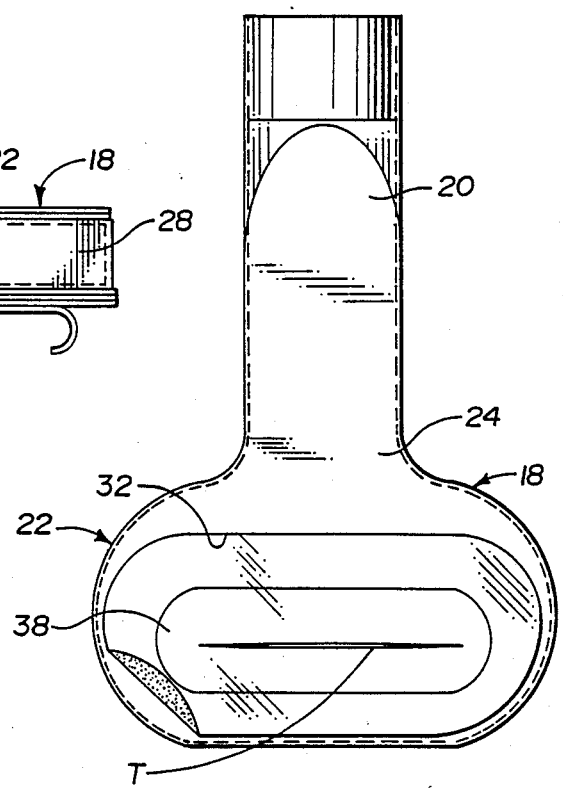
FIG. 3 is a top plan view of the end effector vacuum head in accordance with the present invention.

Collector top wall 24 includes access aperture 32. Collector bottom wall 26 includes access aperture 34 aligned with the top wall access aperture 32. Referring to FIG. 2, a layer of adhesive 36 is carried by the collector top wall 24, and a clear film 38 is removably carried in place over the top access aperture 32 by the adhesive 36. Collector bottom wall 26 includes a first adhesive layer 40 and a clear film 42 removably carried by the first adhesive layer 40. A second adhesive layer 44 having an antiseptic embedded therein is carried by the bottom wall clear film 42. A sterile, peel-off shield 46 is removably carried by the antiseptic adhesive layer 44.

The collector 22 is made of a soft and pliable material so that it will conform to the surface surrounding the surgical site. It will be appreciated that, upon application of a vacuum to the collector 22, the top and bottom wall would be urged together, thereby reducing the volume of internal plenum 30. A plenum support 48 formed from a porous material such as foam urethane is carried within plenum 28, to provide the collector 22 with some rigidity without substantially detracting from the flexibility of the vacuum head 18.

Figure 5:
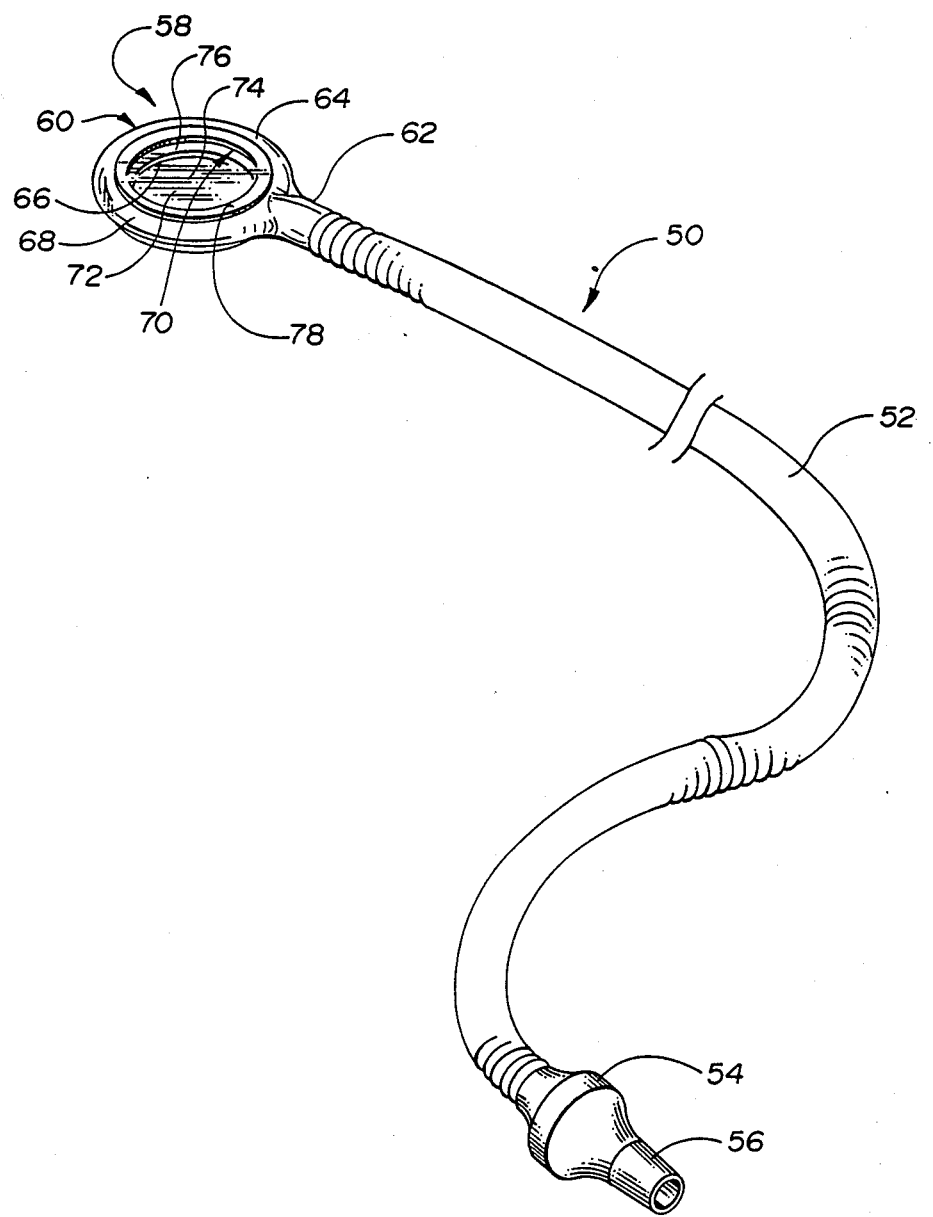
FIG. 5 is a perspective view of a second embodiment of an end effector in accordance with the present invention.

An end effector 50 in accordance with a second embodiment of the present invention is depicted in FIG. 5. The end effector 50 includes a flexible hose 52 similar to the hose 16 depicted and described above in conjunction with the first embodiment of the end effector 12.

The flexible hose 52, however, further includes prefilter chamber 54 and tapered connector 56.

The end effector 50 includes a vacuum head 58. Vacuum head 58 comprises a generally circular collector 60 connected to flexible hose 52 by tubular handle 62. The collector 60 includes collector top wall 64, collector bottom wall 66, and curved sidewall 68 extending between the collector top wall 64 and collector bottom wall 68. Similar to the structure described above in conjunction with the first embodiment 12 of the invention, the collector top, bottom and sidewalls 64, 66, 68 define an internal plenum 70. While the shape of plenum 70 is generally circular as opposed to the generally oval shape of plenum 28, it will be noted that both plenums provide for evacuation of plumes around a complete 360° arc.

Referring again to FIG. 5, it will be seen that end effector 50 includes a top wall access aperture 72, bottom wall access aperture 74, plenum support 76, and top wall clear film 78, similar to the structure described above in conjunction with end effector 12 in accordance with the first embodiment of the invention. Although not explicitly shown in FIG. 5, end effector 50 can also include adhesive layers and a clear film across bottom wall access aperture 74, similar to the structure described and shown in conjunction with end effector 12.

Each of the end effectors 12, 50 described above are advantageously extruded from a single piece of material. That is to say, that collector, tubular handle, flexible hose, and in the case of end effector 50, the prefilter chamber and connector, are formed from a unitary piece of synthetic resin or similar extrudable material.

Figure 4:
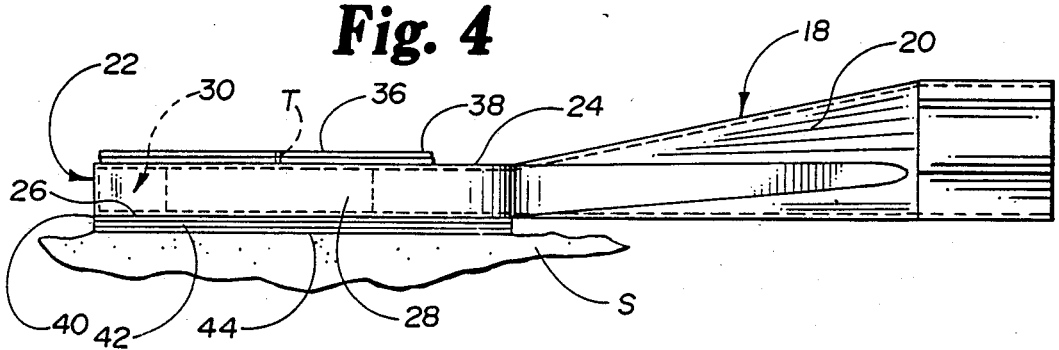
FIG. 4 is a side elevational view of the end effector vacuum head.

The operation of end effector 12 will now be described, it being understood that operation of end effector 50 would be similar. The collector 22 is detachably affixed to the skin S (see FIG. 4) surrounding a surgical site by peeling off the sterile peel-off shield 46 and pressing the adhesive layer 44 carried by bottom wall 26 of the collector 22 against the skin S. It will be appreciated that the flexible nature of vacuum head 18 permits a complete, airtight seal of the bottom wall 26 against the skin S. A tear line T is formed in the clear film 38 carried by the collector top wall 24, and portions of the clear film 42 carried by the collector bottom wall 26 are trimmed away from the immediate vicinity of the surgical site. Alternatively, the clear films 38, 42 carried by the collector top and bottom walls 24, 26, respectively, can be entirely removed. Upon actuation of vacuum generator 14, air is drawn into plenum 28, and is transported through flexible hose 16 and into the filter (not shown) in the vacuum generator 14. Porous plenum support 48 carried within plenum 30 prevents plenum 30 from collapsing in the presence of the vacuum. The plenum support 48 also has the effect of diffusing the vacuum around the plenum 28, thereby drawing air into the plenum 28 around its entire periphery, rather than solely in the vicinity of handle 20. Moreover, drawing air through the larger opening presented by the plenum 28 reduces the noise created by the flow of air into hose 16. Gaseous waste from the interaction of lasers with tissue at the operating at the surgical site is thereby drawn into the plenum 30 and evacuated through flexible hose 16. The plenum support 48, due to its porous nature, also acts as a filter as the smoke plume is drawn through it.

Surgical instruments can be manipulated through the tear line T in clear film 38. Alternatively, the clear film 38 can be completely removed. It will be appreciated that the vacuum, and drawing effect, presented by the plenum to the surgical site is increased by leaving the clear film 38 in place.

Operation of end effector 50 in accordance with the second embodiment of the invention is similar to that described above. The prefilter contained within prefilter chamber 54, however, removes certain of the contaminants within the evacuated smoke prior to entry of the smoke into the vacuum generator 14. The necessity for cleaning the filters within vacuum generator 14 after each use is thereby avoided. Moreover, the entire end effector 50 can be advantageously and hygienically disposed of after a single use, without the necessity of handling the contaminated prefilter.

I claim:

1. An apparatus for removing smoke, airborne particulates gaseous or like by-products of operating procedures producing such by-products from a surgical or other site, comprising:
   a plenum having a top wall, a bottom wall spaced apart from said top wall, a side wall extending between said top and bottom walls and presenting an outer periphery of said plenum, and structure defining a generally open facing presenting an inner periphery of said plenum, said top, bottom, and side walls defining an internal plenum chamber in fluid communication with said open facing;
   vacuum means operably coupled to said plenum for creating a reduced pressure within said plenum chamber, thereby drawing said by-products through said open facing; and
   diffuser means carried within said plenum chamber for maintaining said top and bottom walls in spaced apart relationship and distributing said reduced pressure along the inner periphery of said plenum whereby said by-products are drawn through said open facing from spaced points about said site.

2. The invention as claimed in claim 1, said bottom wall including an adhesive layer for adhesive attachment of said vacuum head around a surgical site.

3. The invention as claimed in claim 1 said top and bottom walls presenting a generally annular shape to said plenum said structure defining said inner periphery comprising structure defining access apertures in said top and bottom walls, said access apertures being adapted for providing access of surgical instruments through said top and bottom walls.

4. The invention as claimed in claim 3, including a top wall transparent film removably carried by said top wall across said top wall access aperture.

5. The invention as claimed in claim 3, including a bottom wall transparent film removably carried by said bottom wall across said bottom wall access aperture.

6. The invention as claimed in claim 1, said vacuum means including a vacuum generator and hose means for operably coupling said plenum chamber to said generator in fluid communicating relationship.

7. The invention as claimed in claim 6, said hose means including a generally flexible hose and a generally rigid handle for coupling said hose to said plenum.

8. The invention as claimed in claim 7, said handle being coupled to said plenum at said plenum side wall, whereby said generally rigid handle provides support for maintaining said top and bottom walls in spaced apart relationship.

9. The invention as claimed in claim 8, said handle being integrally molded with said side wall.

10. The invention as claimed in claim 7, said flexible hose including an internal chamber for carrying a prefilter material within said hose.

* * * * *